(12) United States Patent
Lakso et al.

(10) Patent No.: US 8,852,372 B2
(45) Date of Patent: *Oct. 7, 2014

(54) PANT-TYPE ABSORBENT ARTICLE AND A METHOD FOR PRODUCING PANT-TYPE ABSORBENT ARTICLES

(75) Inventors: Elisabeth Lakso, Stenungsund (SE); Margareta Wennerbäck, Mölnlycke (SE); Jan Wästlund-Karlsson, Mölndal (SE)

(73) Assignee: SCA Hygiene Products AB, Gothenburg (SE)

(*) Notice: Subject to any disclaimer, the term of this patent is extended or adjusted under 35 U.S.C. 154(b) by 1269 days.

This patent is subject to a terminal disclaimer.

(21) Appl. No.: 12/300,413

(22) PCT Filed: May 12, 2006

(86) PCT No.: PCT/SE2006/000563
§ 371 (c)(1),
(2), (4) Date: Nov. 11, 2008

(87) PCT Pub. No.: WO2007/133127
PCT Pub. Date: Nov. 22, 2007

(65) Prior Publication Data
US 2010/0298798 A1 Nov. 25, 2010

(51) Int. Cl.
A61F 13/49 (2006.01)
B32B 37/02 (2006.01)
B32B 25/02 (2006.01)
A61F 13/493 (2006.01)
A61F 13/15 (2006.01)

(52) U.S. Cl.
CPC .......... *A61F 13/15699* (2013.01); *B32B 25/02* (2013.01); *A61F 13/493* (2013.01); *A61F 13/4902* (2013.01); *A61F 13/15804* (2013.01)
USPC .................................. 156/182; 604/385.3

(58) Field of Classification Search
CPC .............. A61F 13/15601; A61F 13/15609; A61F 13/4902; A61F 2013/49022; A61F 13/15593

USPC ......... 604/385.3, 385.24, 386, 394, 395, 396, 604/385.01, 370, 366, 392; 156/164, 161, 156/163, 229, 496, 182, 183, 250, 252, 253, 156/256, 267, 269, 270, 271; 428/297.1
See application file for complete search history.

(56) References Cited

U.S. PATENT DOCUMENTS 4,655,760 A * 4/1987 Morman et al. ......... 604/385.26
4,692,368 A 9/1987 Taylor et al.
(Continued)

FOREIGN PATENT DOCUMENTS

EP 0 650 714 A1 5/1995
EP 0 714 351 B1 6/1996
(Continued)

OTHER PUBLICATIONS

Wennerback et al., Copending U.S. Appl. No. 12/300,398, filed Nov. 11, 2008, entitled "Elastic Laminate and a Method for Producing an Elastic Laminate".
(Continued)

Primary Examiner — (Jackie) Tan-Uyen T Ho
Assistant Examiner — Peter S Vasat
(74) Attorney, Agent, or Firm — Buchanan Ingersoll & Rooney PC

(57) ABSTRACT

A method for producing pant-type absorbent articles, each article including a chassis structure having at least one elastic panel and an integrated absorbent core component, the method including a continuous pant-forming process including forming the chassis structure and incorporating the absorbent core component into the chassis structure. The at least one elastic panel is formed by a) separately producing a two-layer laminate having a first non-elastic fibrous nonwoven web and an elastic film, b) activating the two-layer laminate by incremental stretching in at least one activation direction to render the two-layer laminate elastically stretchable, c) stretching the activated two-layer laminate by 10-200% in the activation direction, d) introducing the two-layer laminate) in the pant-forming process, and e) laminating the elastic film of the stretched two-layer laminate to an elastic or nonwoven chassis component. An absorbent pant-type article produced in accordance with the method.

22 Claims, 7 Drawing Sheets

(56) References Cited

U.S. PATENT DOCUMENTS

| | | | |
|---|---|---|---|
| 4,704,115 A * | 11/1987 | Buell | 604/385.26 |
| 4,771,483 A | 9/1988 | Hooreman et al. | |
| 4,842,596 A | 6/1989 | Kielpikowski et al. | |
| 5,143,679 A | 9/1992 | Weber et al. | |
| 5,156,793 A | 10/1992 | Buell et al. | |
| 5,167,897 A | 12/1992 | Weber et al. | |
| 5,342,343 A | 8/1994 | Kitaoka et al. | |
| 5,422,172 A * | 6/1995 | Wu | 442/62 |
| 5,576,090 A | 11/1996 | Suzuki | |
| 5,592,690 A | 1/1997 | Wu | |
| 5,634,216 A | 6/1997 | Wu | |
| 5,711,832 A * | 1/1998 | Glaug et al. | 156/73.1 |
| 5,733,628 A | 3/1998 | Pelkie | |
| 5,855,574 A | 1/1999 | Kling et al. | |
| 5,855,999 A | 1/1999 | McCormack | |
| 5,861,074 A | 1/1999 | Wu | |
| 5,939,178 A | 8/1999 | Boich | |
| 5,964,973 A | 10/1999 | Heath et al. | |
| 5,997,981 A | 12/1999 | McCormack et al. | |
| 6,054,727 A | 4/2000 | Voss | |
| 6,149,637 A | 11/2000 | Allen et al. | |
| 6,313,372 B1 | 11/2001 | Suzuki | |
| 6,506,698 B1 * | 1/2003 | Quantrille et al. | 442/361 |
| 6,673,980 B1 * | 1/2004 | Varona et al. | 604/367 |
| 6,911,106 B2 | 6/2005 | Otsubo et al. | |
| 7,008,496 B2 | 3/2006 | Morman | |
| 8,545,654 B2 * | 10/2013 | Lakso et al. | 156/182 |
| 2002/0002021 A1 | 1/2002 | May et al. | |
| 2003/0024625 A1 | 2/2003 | McAmish et al. | |
| 2003/0105446 A1 | 6/2003 | Hutson et al. | |
| 2004/0040642 A1 | 3/2004 | Otsubo et al. | |
| 2004/0102754 A1 | 5/2004 | Morman et al. | |
| 2004/0108043 A1 | 6/2004 | Otsubo | |
| 2004/0112509 A1 | 6/2004 | Morman | |
| 2004/0127528 A1 | 7/2004 | Eriksson et al. | |
| 2004/0133180 A1 * | 7/2004 | Mori et al. | 604/385.25 |
| 2004/0158217 A1 | 8/2004 | Wu et al. | |
| 2004/0192140 A1 | 9/2004 | Schneider et al. | |
| 2004/0241389 A1 | 12/2004 | Chung et al. | |
| 2004/0243089 A1 | 12/2004 | Veith et al. | |
| 2005/0101216 A1 | 5/2005 | Middlesworth et al. | |
| 2005/0126689 A1 * | 6/2005 | Thorson et al. | 156/164 |
| 2005/0136778 A1 | 6/2005 | Thomaschefsky et al. | |
| 2005/0230037 A1 | 10/2005 | Jenquin et al. | |
| 2005/0257881 A1 | 11/2005 | Coose et al. | |
| 2006/0083900 A1 | 4/2006 | Ashraf | |
| 2006/0144503 A1 | 7/2006 | Carr | |
| 2006/0148358 A1 | 7/2006 | Hall et al. | |
| 2006/0148361 A1 | 7/2006 | Ng et al. | |
| 2006/0254708 A1 | 11/2006 | Wada et al. | |
| 2008/0009817 A1 | 1/2008 | Norrby | |
| 2009/0038751 A1 | 2/2009 | Hermansson et al. | |
| 2009/0208703 A1 | 8/2009 | Wennerbäck et al. | |
| 2009/0326503 A1 | 12/2009 | Lakso et al. | |
| 2013/0240123 A1 | 9/2013 | Lakso et al. | |

FOREIGN PATENT DOCUMENTS

| | | | |
|---|---|---|---|
| EP | 0 715 351 A1 | 6/1996 | |
| EP | 1 688 113 A1 | 8/2006 | |
| JP | 5-245961 A | 9/1993 | |
| JP | 6-047808 A | 2/1994 | |
| JP | 8-280741 A | 10/1996 | |
| JP | 9-078431 A | 3/1997 | |
| JP | 9-503167 A | 3/1997 | |
| JP | H09-504488 A | 5/1997 | |
| JP | 2003-025471 A | 1/2003 | |
| JP | 2004-305771 A | 11/2004 | |
| JP | 2005-511345 A | 4/2005 | |
| JP | 2005-178365 A | 7/2005 | |
| JP | 2008-503315 A | 2/2008 | |
| JP | 2008-514269 A | 5/2008 | |
| RU | 2140855 C1 | 11/1999 | |
| RU | 2205757 C2 | 6/2003 | |
| RU | 2283238 C2 | 9/2006 | |
| RU | 2006122606 A | 1/2008 | |
| WO | WO 85/05254 A1 | 12/1985 | |
| WO | WO 95/04654 A1 | 2/1995 | |
| WO | WO 95/18589 A1 | 7/1995 | |
| WO | WO 00/45764 A1 | 8/2000 | |
| WO | WO 03/047488 A1 | 6/2003 | |
| WO | WO 03/070140 A1 | 8/2003 | |
| WO | WO 2004/078083 A1 | 9/2004 | |
| WO | WO 2005/122985 A1 | 12/2005 | |
| WO | WO 2006/007200 A2 | 1/2006 | |
| WO | WO 2006/036090 A1 | 4/2006 | |
| WO | WO 2006/093440 A1 | 9/2006 | |
| WO | WO 2008/060204 | 5/2008 | |
| WO | WO 2008/060205 | 5/2008 | |

OTHER PUBLICATIONS

Lakso et al., Copending U.S. Appl. No. 12/300,357, filed Nov. 11, 2008, entitled "Pant-Type Absorbent Article and a Method for Producing Pant-Type Absorbent Articles".

Office Action issued on Nov. 17, 2009 in Copending U.S. Appl. No. 12/300,398 in the name of Wennerback et al. and titled "Elastic Laminate and a Method for Producing an Elastic Laminate".

Office Action issued on Mar. 8, 2010 in copending U.S. Appl. No. 12/300,398 in the name of Wennerback et al. and titled "Elastic Laminate and a Method for Producing an Elastic Laminate".

English language translation of an Official Action issued on Jun. 28, 2011 by the Japanese Patent Office in corresponding Japanese Patent Application No. 2009-509475.

Official Action of Aug. 30, 2012 issued in U.S. Appl. No. 12/300,357, 19 pages, U.S. Patent and Trademark Office.

Official Action of Mar. 27, 2012 issued in U.S. Appl. No. 12/300,357, 18 pages, U.S. Patent and Trademark Office.

Notice of Reasons for Rejection in corresponding Japanese Patent Application No. 2009-510913, mailed Apr. 26, 2011, (1 page), and English-language translation thereof (5 pages), Japan Patent Office, JP.

English-language translation of Office Action in Japanese Patent Application No. 2009-510919, mailed Jan. 17, 2012, 3 pages, Japan Patent Office, JP.

Official Decision of Grant dated Jun. 1, 2010 issued in corresponding RU Patent Application No. 2008148969 (2 pages), and English-language translation thereof (4 pages), Russian Patent Office, RU.

Supplemental European Search Report in European Patent Application No. 06747782, Aug. 19, 2011, seven pages, EPO, Munich, DE.

Supplemental European Search Report in European Patent Application No. 06733408.6, May 17, 2011, seven pages, EPO, Munich, DE.

Notice of Allowance issued on Jan. 31, 2014 in copending Application No. US-2009/0208703 A1, 11 pages, U.S. Patent and Trademark Office.

PCT/ISA/210, Dec. 12, 2006.
PCT/ISA/237, Dec. 12, 2006.
PCT/IPEA/408, Jun. 19, 2008.

* cited by examiner

PANT-TYPE ABSORBENT ARTICLE AND A METHOD FOR PRODUCING PANT-TYPE ABSORBENT ARTICLES

PRIORITY

This application is a national stage application of PCT/SE2006/000563, filed 12 May 2006.

TECHNICAL FIELD

The disclosure pertains to a method for producing pant-type absorbent articles, each article including a chassis structure having at least one elastic panel and an integrated absorbent core component, the method including a continuous pant-forming process comprising forming the chassis structure and incorporating the absorbent core component into the chassis structure.

BACKGROUND ART

Pant-type absorbent articles include a pant-shaped chassis structure and an absorbent core component integrated with the chassis. A major objective when designing pant articles is to make them resemble ordinary underwear as closely as possible. Hence, absorbent articles such as pant diapers, sanitary pants and incontinence pants are designed to fit comfortably and snugly about the wearer. It is desirable that the articles are capable of being pulled up and down over the hips of the wearer in the manner of a pair of underpants to allow the wearer or caregiver to easily remove a soiled article and to replace it with a new clean article. For these reasons, the article chassis is usually made of a material that is elastically stretchable, at least in the areas intended to be applied over the wearer's hips. Furthermore, it is desirable that the chassis surrounding the absorbent parts of the pant article is permeable to air and vapour, i.e. that it is breathable. A breathable article prevents moisture from remaining on the skin of the wearer and is more comfortable and less warm to wear than a non-breathable article. It is also beneficial if the article is soft, smooth and textile-like, so that it does not chafe the skin of the wearer and so that it resembles ordinary underwear as closely as possible.

Moreover, it is desirable that the absorbent pant article can be pulled up over the hips of a wearer without rupturing. A common problem is that the wearer or the caregiver tears the pant by running the fingers through the material when trying to get a good grip for pulling up or removing the pant.

A previously used elastic material for pant articles is a laminate comprising an elastic film sandwiched between two layers of non-elastic nonwoven. In order to render the laminate elastically stretchable, it is subjected to an activation treatment. A three-layer, activated laminate is disclosed in International Patent Application No. WO 03/047488. The activated laminate is produced by incrementally stretching an elastic film layer between two non-elastic cloth-like layers. Incremental stretching is carried out by passing the laminate between intermeshing gear rollers. Activation of elastic laminates by incremental stretching is also disclosed in U.S. Pat. Nos. 5,143,679, 5,156,793 5,167,897, 5,422,172, 5,592,690, 5,634,216 and 5,861,074. The non-elastic cloth-like layers are fully or partially broken or torn during the activation process so that the elasticity of the laminate after activation is governed mainly by the elasticity of the elastic film layer. In the three-layer laminate in WO 03/047488, the non-elastic layers are completely broken so that the elasticity of the activated laminate is substantially the same as the elasticity of the elastic film layer.

The disclosed laminates have excellent comfort properties and are soft, breathable and elastic. However, a major disadvantage with the known laminates is that the activation process at least partially breaks and destroys the cloth-like layers resulting in a material having decreased tensile strength and puncture resistance in a direction perpendicular to the direction of elasticity of the material. When used as a chassis component in a disposable pant article, the material is easily torn when exposed to the forces arising when putting on or pulling off the pant article. This tearing problem is particularly pronounced for female wearers or caregivers who often have long fingernails that may penetrate and tear the pant material.

Another problem with the previously known three-layer laminates is that they have a pre-determined extensibility and elasticity. However, it is often desirable to have different elasticity in different parts of a pant-type article. In order to accomplish this, it is necessary to supplement the elastic panels created from the three-layer laminate with additional elastic elements or to make different parts of the diaper chassis from different laminates. However, all such extra components are costly and complicate the manufacturing process since they require additional process steps, thus incurring additional processing costs. Moreover, the resulting absorbent articles have a great number of seams and joins, making them appear less like ordinary underwear. It is a desirable to keep the number of seams and joins to a minimum both for manufacturing reasons and since they may cause discomfort such as chafing of a wearer's skin.

Hence, there exists a need for an improved pant-type absorbent article having a chassis including one or more elastically stretchable textile-like components. Moreover, there exists a need for a simple and efficient process for producing such an absorbent article.

OBJECTS AND SUMMARY

Accordingly, an object of the disclosure is to provide an elastically stretchable pant-type absorbent article having improved tensile strength in the elastic parts of the pant chassis. A further object of the disclosure is to provide a simple and economic method for producing an elastically stretchable pant-type article having improved tensile strength and puncture resistance. It is also an object of the disclosure to provide a method having high processing flexibility and variability to allow simple adaptation of the method to different product designs.

There is provided a method for producing pant-type absorbent articles having improved tensile strength and puncture resistance. The articles include a chassis structure having at least one elastic panel and an integrated absorbent core component. The method comprises two part processes and includes a continuous pant-forming process comprising forming the chassis structure and incorporating the absorbent core component into the chassis structure.

The at least one elastic panel is formed by a) separately producing a two-layer laminate comprising a first non-elastic fibrous nonwoven web and an elastic film, b) activating the two-layer laminate by incremental stretching in at least one direction to render the two-layer laminate elastically stretchable, c) stretching the activated two-layer laminate by 10-200% in at least one direction, d) introducing the two-layer laminate in the pant-forming process, and e) laminating the elastic film of the stretched two-layer laminate to an elastic or non-elastic nonwoven chassis component web.

Accordingly, the method involves forming a two-layer laminate and introducing the laminate in a pant-forming process so as to create a final three-layer panel-forming laminate at the same time as producing the pant-type article. In this manner, the resulting three-layer laminate will have much higher resistance to rupturing or breaking than the previously used three-layer laminates that have been completely formed prior to activation. The method is also advantageous in that it offers high process flexibility since the two-layer laminate may be laminated only to those portions of the nonwoven chassis component web where elasticity is desired. Moreover, it is possible to use different two-layer laminates in different portions of the chassis web and to laminate the two-layer laminate to a nonwoven chassis component under different degrees of stretch in different portions of the chassis web.

The two-layer elastic laminate is preferably in the form of one or more running webs that are continuously introduced in the pant-forming process.

Alternatively, the laminate can be cut and shaped into separate elements that are used to produce elastic portions in the disposable pant article.

The two-layer laminate can be attached to the elastic or non-elastic nonwoven chassis component web to produce the elastic three-layer laminate before joining the three-layer laminate to other components in the pant-forming process or can be laminated with the nonwoven chassis component web at a later stage in the pant-forming process. If two or more two-layer laminate webs are used in the pant-forming process, the webs can be formed by dividing a single original web into the desired number of webs. The web may be divided before or after lamination to a nonwoven chassis component web. Alternatively, the individual webs can be separately produced and introduced into the process.

It is further possible to:

a) produce first and second three-layer elastic laminate webs by laminating an activated, stretched two-layer laminate to a nonwoven web, b) joining a first web of the three-layer elastic laminate to a first edge of a continuous central nonwoven chassis web, and c) joining a second web of the three-layer elastic laminate to a second edge of the continuous central nonwoven chassis web to form a compound chassis web.

The first and second three-layer elastic laminate webs may be produced as a single three-layer laminate that is subsequently split to produce first and second three-layer laminate webs.

In another embodiment of the method, the pant-forming process comprises:

a) laminating a first web of the activated stretched two-layer elastic laminate to a portion of a first continuous nonwoven chassis web at a distance from a first edge on the first continuous nonwoven chassis web, b) laminating a second web of the activated, stretched two-layer laminate to a portion of a second continuous nonwoven chassis web at a distance from a first edge on the second continuous nonwoven chassis web, c) joining the first edge on the first continuous nonwoven chassis web to the first edge on the second continuous nonwoven chassis web to form a compound chassis web.

The process further offers the advantage making it possible to use the same pre-fabricated two-layer laminate to create panels having different extensibility, flexibility and elasticity. This is achieved by selecting the degree of stretching of the two-layer laminate in the laminating step in the pant-forming process and by selecting the material used for the nonwoven chassis component. Hence, different two-layer laminates and different degrees of stretching can be used in the process to form a diaper chassis having different elasticity in different portions.

In this context, an elastic material is defined as a material having a permanent elongation after relaxation of less than 10% after the material has been subjected to an elongation of 30% in the elasticity test specified in the description.

A non-elastic material is a material that does not fall within the definition of an elastic material. Accordingly, a non-elastic material as used herein is a material that may be stretchable or non-stretchable. In the case of a stretchable material, the material has a permanent elongation after stretching and relaxation of more than 10% after having been subjected to an elongation of 30% as determined according to the elasticity test.

The degree of stretching of the two-layer laminate when attaching it to the nonwoven chassis component is a major factor in determining the elasticity of the final three-layer laminate produced in the pant-forming process. Other factors that influence the elasticity of the final three-layer laminate are the flexibility and extensibility of the nonwoven chassis component. The amount of bonding between the two-layer laminate and the second nonwoven web does also affect the flexibility and elasticity of the final three-layer laminate. Accordingly, a large bonded area will decrease the elasticity in the final laminate while sparsely distributed bonding points will have a very small or negligible influence on the elasticity.

The elastic film in the two-layer laminate is preferably perforated in order to provide breathability in the laminate. This can be achieved directly in conjunction with the lamination process if, for instance, the first nonwoven web is bonded to the elastic film by means of extrusion coating. The perforating step can be carried out by passing the combined elastic layer and nonwoven web over a vacuum lamination drum while the elastic layer is in a molten or semi-molten state. Such a process is disclosed in U.S. Pat. No. 5,733,628 and results in the elastic film being formed into a three-dimensional apertured laminate layer.

Alternatively, the elastic film can be a prefabricated perforated film that is bonded to the first nonwoven web by any suitable means such as adhesively, thermally or with ultrasonic welding.

The activation step involves incremental stretching of the two-layer laminate so that the non-elastic material is broken or torn, at least partially. Activation can be carried out by means of heated or non-heated intermeshing gear rollers having circumferentially arranged teeth that intermesh and thereby stretch the laminate. The activation step allows the laminate to be subsequently stretched without being appreciably restrained by the nonwoven web. The degree of breaking of the nonwoven material determines the maximum possible elongation for the resulting laminate. If the nonwoven material is completely broken in the activation process, the laminate will have substantially the same maximum elongation as the elastic film layer.

When carrying out the second laminating step in the pant-forming part of the method, the two-layer laminate is stretched in at least one direction by 10-200% of its initial, non-stretched extension. Preferably, the two-layer laminate is stretched in the machine direction, MD. By choosing and controlling the amount of stretch, it is possible to obtain a selected elasticity in the end laminate. The two-layer laminate is preferably stretched by 35-180% of its non-stretched extension, more preferably by 50-150% of its non-stretched extension and most preferably by 70-120% of its non-stretched extension during lamination with the second nonwoven web.

The amount of stretching of the two-layer laminate is specified as a percentage of the initial, non-stretched extension of the laminate in the direction of stretch. Accordingly, a laminate having a first, non-stretched length of 1 m and being stretched by 50% has a second, stretched length of 1.5 m.

The activated two-layer laminate can be adhesively bonded to the nonwoven chassis component. Alternatively, the activated two-layer laminate can be thermally or ultrasonically bonded to the nonwoven chassis component. Thermal or ultrasonic bonding can be in the form of discreet bonds such as spot bonds or line bonds. By selecting a bond pattern of sparsely distributed spot bonds, it is possible to achieve a higher flexibility in the resulting laminate than with a bond pattern occupying a large proportion of the interface between the bonded layers.

In accordance with a further embodiment, the pant-forming process comprises the steps of:
 a) laminating the elastic film of a first web of the activated, stretched two-layer laminate to a first portion of a continuous nonwoven chassis web, and
 b) laminating the elastic film of a second web of the activated stretched two-layer elastic laminate to a second portion of the nonwoven chassis web to form a compound chassis web.

By a compound chassis web is meant a web comprising two or more components and from which web a pant-type article chassis is formed.

The first web of the activated stretched two-layer elastic laminate may be laminated to a first portion of the continuous nonwoven chassis web at a distance from a first edge on the continuous nonwoven chassis web, and the second web of the activated, stretched two-layer laminate may be laminated to a second portion of the continuous nonwoven chassis web at a distance from a second edge on the continuous nonwoven chassis web. In this manner, elastic waist features can be formed along the first and second edges of the continuous nonwoven chassis web by joining elastic members to the continuous nonwoven chassis web at a first edge portion between the first edge of the continuous nonwoven chassis web and the first web of the activated stretched two-layer elastic laminate and at a second edge portion between the second edge of the continuous nonwoven chassis web and the second web of the activated stretched two-layer elastic laminate and by folding the first and second edge portions of the continuous nonwoven chassis web to enclose the elastic means. Hence, the portions of the continuous nonwoven chassis web extending beyond the elastic laminate webs at the edges of the nonwoven chassis web can be used to form an elastic waist feature that is an integral part of the compound chassis web.

In the finished pant-type absorbent article, the part of the nonwoven chassis web that is arranged centrally between the two-layer laminate webs will form a crotch panel and the laminated elastic web portions on either side of the central part of the chassis web will form elastically extensible front and back panels. The nonwoven chassis web can be an elastic or non-elastic web.

The core component can be placed on the compound chassis web with a central portion extending over the central nonwoven chassis web and with end portions of the core component extending in over each of the two-layer laminate webs.

According to a further embodiment, the pant-forming process comprises:
 a) joining a first web of the activated, stretched two-layer laminate to a first edge of a continuous central nonwoven chassis web,
 b) joining a second web of the activated stretched two-layer elastic laminate to a second edge of the central nonwoven chassis web to form a compound chassis web,
 c) laminating a first nonwoven web to the elastic film of the first web of the activated stretched two-layer laminate, and
 d) laminating a second nonwoven web to the elastic film of the second web of the activated, stretched two-layer laminate.

The core component may be joined to the chassis web before or after the activated stretched two-layer elastic laminate webs are laminated with the first and second nonwoven webs.

Particularly in an embodiment where the core component is placed on the chassis web before the final laminating step, it may be beneficial if the first and second nonwoven webs are provided with cut-outs corresponding in size and shape to the portions of the core component that are arranged in overlap with the first and second nonwoven webs, the cut-outs being brought into register with the core components. In this manner it is avoided that the portions of the core component that extend in over the elastic two-layer laminate are covered by the second nonwoven webs in the laminating step.

In a further embodiment, the pant-forming process comprises:
 a) joining a first web of the activated, stretched two-layer laminate to a first edge of a continuous central nonwoven chassis web,
 b) joining a second web of the activated stretched two-layer elastic laminate to a second edge of the central nonwoven chassis web to form a compound chassis web,
 c) attaching leg elastic members to the compound chassis web, and
 d) laminating a nonwoven web to the compound chassis web, the nonwoven web covering the first and second two-layer elastic laminate webs and the leg elastic members.

This embodiment is advantageous in that it offers good securement and coverage of the leg elastic members at the same time as the elastic panel portions of the chassis web are provided with reinforcement.

The method preferably also includes arranging an elastic waist feature along at least one of the edges of the chassis.

The elastic waist feature can be joined to the chassis web as a separate component that is prefabricated or is manufactured in line with the pant-forming process. The elastic waist feature is preferably continuously joined to or arranged on the chassis web and may be supplied as an elastic band, of any suitable kind, such as elastic laminates, elastic foam strips, elastic nonwovens, non-elastic materials that have been elasticised with elastic threads or strings, etc. A commonly used elastic waist feature is made by attaching elastic elements such as threads, bands or strings in a pre-tensioned state between two layers of nonwoven, non-elastic material. All commonly used elastic materials such as natural or synthetic rubber elastic foam, etc. can be employed. A waist feature of this type may be formed from two separate layers of nonwoven or may be made from a single layer of nonwoven that is folded into a two-layer structure. It is also possible to use the activated two-layer laminate to create an elastic waist feature. The elastic waist feature preferably has a higher elastic tension than the elastic panel portions.

In an alternative embodiment, the elastic waist feature is an integral part of the chassis web. In this embodiment, the elastic waist feature may be formed by folding an edge portion of an elastic or non-elastic part of the chassis web and attaching elastic elements between the folded portions of the chassis web. Typically, the elastic waist feature is formed by folding a portion of the nonwoven chassis web component that is an extension of one of the nonwoven layers in the elastic three-layer laminate produced. It is also possible to attach elastic elements to a layer of the chassis web and leave the elastic elements non-covered, or covered by a separate web. If the elastic waist feature incorporates the elastic laminate web, the elastic laminate web may be folded to create a double laminate portion having higher elastic retraction force than the non-folded portion of the part of the chassis web including only a single two-layer laminate web. The folded elastic laminate web may be supplemented by additional elastic elements.

The activated two-layer laminate may be stretched in at least one direction by 35-180% of its non-stretched extension, more preferably by 50-150% of its non-stretched extension and most preferably by 70-120% during lamination with the nonwoven chassis component.

The method may further include any conventional pant-forming production steps such as one or more of the following production steps:
a) cutting the chassis web to form leg openings,
b) folding the chassis web together with the integrated absorbent core component,
c) forming side joins in the folded web, and
d) separating individual pant-type absorbent articles from the chassis by cutting at the side joins.

Side joins are often arranged in a pant-type article to connect the article's front portion to the rear portion and to form a pant having a waist opening and leg openings. Usually, the side joins are intended to be arranged at the user's hips during use of the absorbent pants, but it is also known to arrange side joins more to the front of the article. The side joins are preferably designed so that they can withstand the tensile forces which arise when the article is being put on and is being worn, but such that they can be torn apart or opened in a controlled manner when the absorbent pants are taken off or to check if the article needs changing. In the latter instance, the side joins are preferably reclosable joins, as known in the art.

A pant-type absorbent article also comprises a chassis structure comprising a front panel having a front end edge and first and second side edges, a back panel having a back end edge and first and second side edges and a crotch panel arranged between the front and back panels and front and back waist panels arranged at the front and back panels, respectively and forming a waist-band on the absorbent article, and a core component being integrated with the chassis structure, the first and second side edges of the front panel being joined by edge joins to the corresponding first and second side edges of the back panel. At least one of the front and back panels comprises a two-layer elastic laminate comprising a first non-elastic fibrous nonwoven web and an elastic film and a nonwoven chassis component that has been laminated to the elastic film of the two-layer elastic laminate while the two-layer elastic laminate was stretched by 10-200%. The two-layer elastic laminate was preferably stretched by 35-180% of its non-stretched extension, more preferably by 50-150% of its non-stretched extension and most preferably by 70-120% during lamination to the nonwoven chassis component.

The elastic three-layer laminate chassis portions preferably form the front and the back panels of the pant-type diaper. However, it is possible to make only parts of the respective front and back panels of the elastic three-layer laminate. In such embodiments, at least 20%, preferably at least 25%, more preferably at least 30% and most preferably at least 40% of the total surface area of the chassis is constituted by the elastic three-layer laminate. As an example, the elastic two-layer laminate may be applied only to those parts of the front and back panels that are intended to lie over the wearer's hips and thus form elastic side panels. It is also possible to design a pant-type article without any overlap between the region in which the core component is applied and the elastic laminate material in the front and back panels.

The first non-elastic fibrous nonwoven web and/or the nonwoven chassis component may comprise thermoplastic fibres. The nonwoven webs will typically be incorporated in joins and seams in the disposable pant-type article. Hence, it is highly desirable that the nonwoven webs be weldable by heat or by ultrasonic welding processes. Examples of suitable polymers for use in the nonwoven webs are polyethylene, polyesters, polypropylene and other polyolefin homopolymers and copolymers. Particularly well suited nonwoven webs are those comprising thermoplastic fibres that are a blend of polypropylene and polyethylene fibres. The weldable nonwoven webs have a high content of thermoplastic fibres and contain at least 50% thermoplastic fibres and preferably at least 80% thermoplastic fibres.

A suitable type of nonwoven webs for use particularly as the nonwoven chassis component is a creped nonwoven. Creped nonwovens generally have greater extensibility and flexibility than non-creped nonwovens. By choosing a creped nonwoven for the nonwoven chassis component, it is possible to achieve a final three-layer laminate in the panty-type article that is more conformable and extensible than is possible with a non-creped nonwoven. The creped nonwoven makes it easier for the three-layer laminate to contract after elongation, thus increasing the elasticity when compared to a corresponding laminate having a non-creped second nonwoven layer. If desired, the non-elastic nonwoven web in the two-layer laminate can also be a creped nonwoven.

The elastic film used for producing the two-layer laminate may be of any suitable elastic polymer, natural or synthetic. One example of an elastic film that has proven to provide good elasticity and breathability is an apertured three-layer elastomeric film with the composition polyethylene-styrene/ethylene/butadiene/styrene-polyethylene (PE-SEBS-PE).

The elastic two-layer laminate used in the pant-forming process is composed of a layer of fibrous material and an elastic layer. The fibrous layer is chosen so that it provides a soft and cloth-like feel and appearance to the laminate. Examples of suitable materials are meltblown webs, spunbond materials, and creped nonwovens, as set out above. Such materials are also suitable for the nonwoven chassis component to which the two-layer laminate is attached. However, any soft, flexible and preferably extensible nonwoven materials and nonwoven laminates may be used, such as Spunbond-Meltblown-Spunbond-laminates (SMS), carded and spunlaced materials.

The basis weight of the nonwoven web used in the two-layer laminate is suitably from 10-80 $g/m^2$ and preferably from 13-50 $g/m^2$. Examples of suitable polymers used in the fibrous material are polyethylene, polyesters, polypropylene and other polyolefin homopolymers and copolymers. Natural fibres, for example cotton, may also be used as long as they provide the desired properties. A mixture of polymers can contribute to a higher flexibility of the nonwoven layer, and through this, give the nonwoven material a higher elongation at maximum load. A mixture of polyethylene and polypropylene polymers has proven to provide good results in this respect. However, nonwovens having different fibre mixtures may also be used.

The elastic layer is preferably an apertured elastic film. The elastic layer may have a basis weight of between 10 and 120 g/m$^2$, preferably between 15 and 60 g/m$^2$. The elastic layer may be of any suitable elastic polymer, natural or synthetic. Some examples of useful materials for the elastic layer are low crystallinity polyethylenes, metallocene-catalyzed low crystallinity polyethylenes, ethylene vinyl acetate copolymers (EVA), polyurethane, polyisoprene, butadiene-styrene copolymers, styrene block copolymers, such as styrene/isoprene/styrene (SIS), styrene/butadiene/styrene (SBS), or styrene/ethylene-butadiene/styrene block copolymer. Blends of these polymers may also be used as well as other modifying elastomeric or non-elastomeric materials. One example of a suitable elastic film is an apertured three-layer elastomeric film with the composition polyethylene-styrene/ethylene/butadiene/styrene-polyethylene (PE-SEBS-PE).

The elastic two-layer laminate can, for instance, be manufactured and activated according to either of the methods disclosed in WO 03/047488 or EP 0 714 351 by applying the nonwoven web to one side of the film. The nonwoven web and the film may be extrusion bonded or may be bonded by adhesive. The two-layer laminate is incrementally stretched to activate the elasticity of the film layer. Incremental stretching can be made to a point below the elongation at peak load of the nonwoven web to retain some strength in the nonwoven web. Alternatively, the stretching may be carried out so that the nonwoven is completely torn, as disclosed in WO 03/047488.

When laminating the two-layer laminate to the nonwoven chassis component, a three-layer laminate is created having a smooth face on the surface where the two-layer laminate is arranged and a somewhat gathered, puckered face on the opposing surface, where the chassis component is arranged. Accordingly, depending on the order of the layers in the produced pant-type article, the three-layer laminate can be oriented with the smooth face on the inside of the article and the irregular face facing outwardly. In this manner, the skin-contacting parts of the laminate will be particularly soft, smooth and non-chafing against the wearer's skin. However, it is alternatively possible to arrange the laminate with the smooth face on the outside of the absorbent article. In this manner, an absorbent article having a smooth surface in contact with any clothing worn over the absorbent article is obtained. Such an embodiment can be advantageous when the article is a pair of sanitary pants or incontinent pants for adults. The smooth surface of the laminate is aesthetically pleasing and will be less conspicuous when the absorbent article is worn under thin or tight-fitting garments.

BRIEF DESCRIPTION OF DRAWINGS

The disclosure will in the following be described in connection to preferred embodiments and in greater detail with reference to the appended exemplary drawings, wherein.

DETAILED DESCRIPTION OF THE PREFERRED EMBODIMENTS

Figure 1:
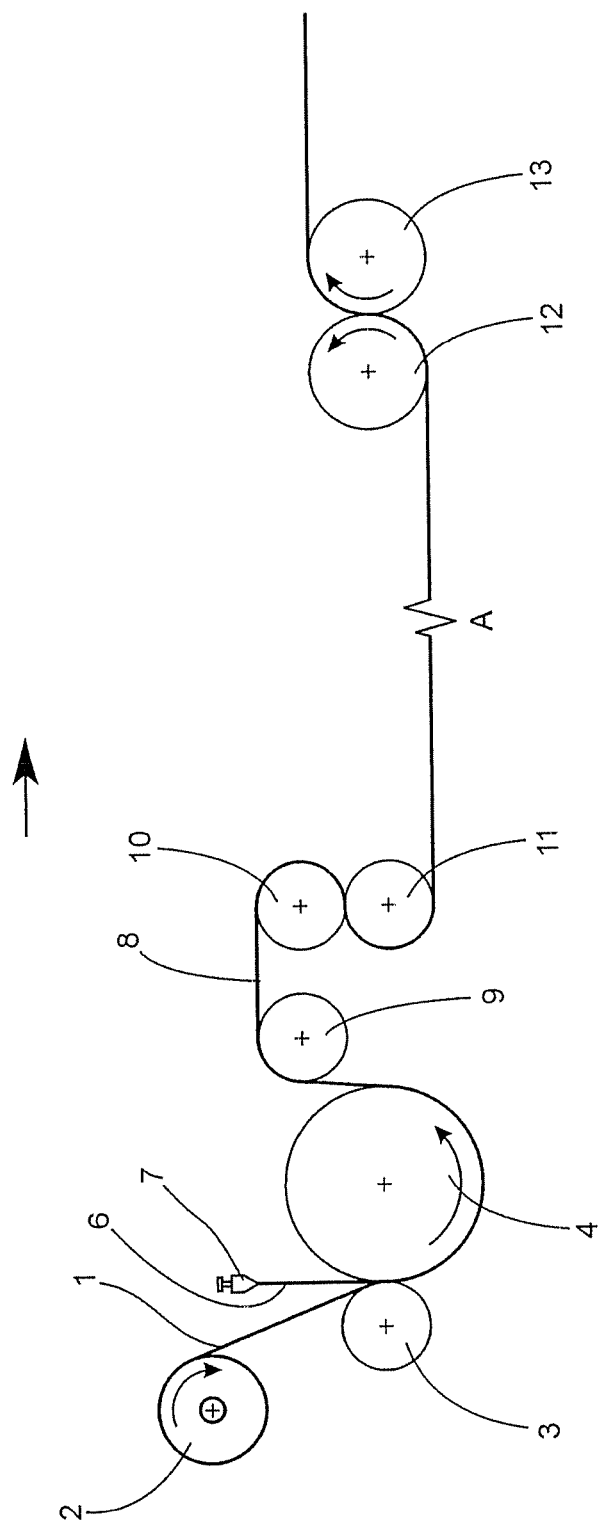
FIG. 1 shows schematically a method for producing a two-layer elastic laminate.

FIG. 1 shows schematically a method for producing an elastically stretchable two-layer laminate that can be incorporated in a pant-type absorbent article.

A nonwoven web 1 is fed from a storage roll 2 into a bonding nip between a rubber roll 3 and a metal roll 4. A molten elastic film-forming polymer 6 is extruded through a die 7 into the nip and the nonwoven web 1 and the elastic film forms a two-layer laminate 8 that is taken off at a roller 9.

The metal roll 4 in the bonding nip is preferably an apertured suction roll so that three-dimensional forming and aperturing of the extruded elastic film 6 is achieved simultaneously with bonding of the film 6 to the nonwoven web 1.

The two-layer laminate 8 is subsequently activated by passing the laminate between intermeshing gear rollers 10,11 so that the laminate 8 is subjected to incremental stretching. A number of different stretching techniques exist, as set out in EP 0 714 351. Depending on the design of the intermeshing gear rollers, the incremental stretching can be made to stretch the laminate diagonally, in the machine direction (MD) or in the cross direction (CD). The amount of breakage of the nonwoven web caused by the incremental stretching can be controlled by adjusting the intermeshing depth of the teeth or intermeshing elements on the gear rollers. The incremental stretching releases or activates the elasticity of the elastic film and allows the two-layer laminate 8 to be elastically extensible. In the laminates of the disclosure, activation will usually involve tearing or breaking of the nonwoven web principally along deformation lines parallel with the CD and perpendicular to the MD.

After activation the laminate 8 is preferably rolled up in an un-tensioned state on a storage roll and allowed to relax for a period of time. The relaxation step is represented by showing the production line as broken at A in FIG. 1. Intermediate storage and relaxation may be particularly beneficial if the production speed in the lamination process is lower than the production speed in the pant-forming process or when the two-layer laminate is bought from an external supplier and used it in the pant-forming process in accordance with the disclosure.

The activated and preferably relaxed laminate 8 is subsequently stretched by passing between a pair of rollers 12,13 driven at different speeds. The laminate 8 is stretched in at least one direction to 10-200% of its initial, non-stretched extension before it is introduced in a pant-forming process and laminated to a third component web. By choosing and controlling the amount of stretch, it is possible to obtain a selected elasticity in the three-layer end laminate.

Figure 2:
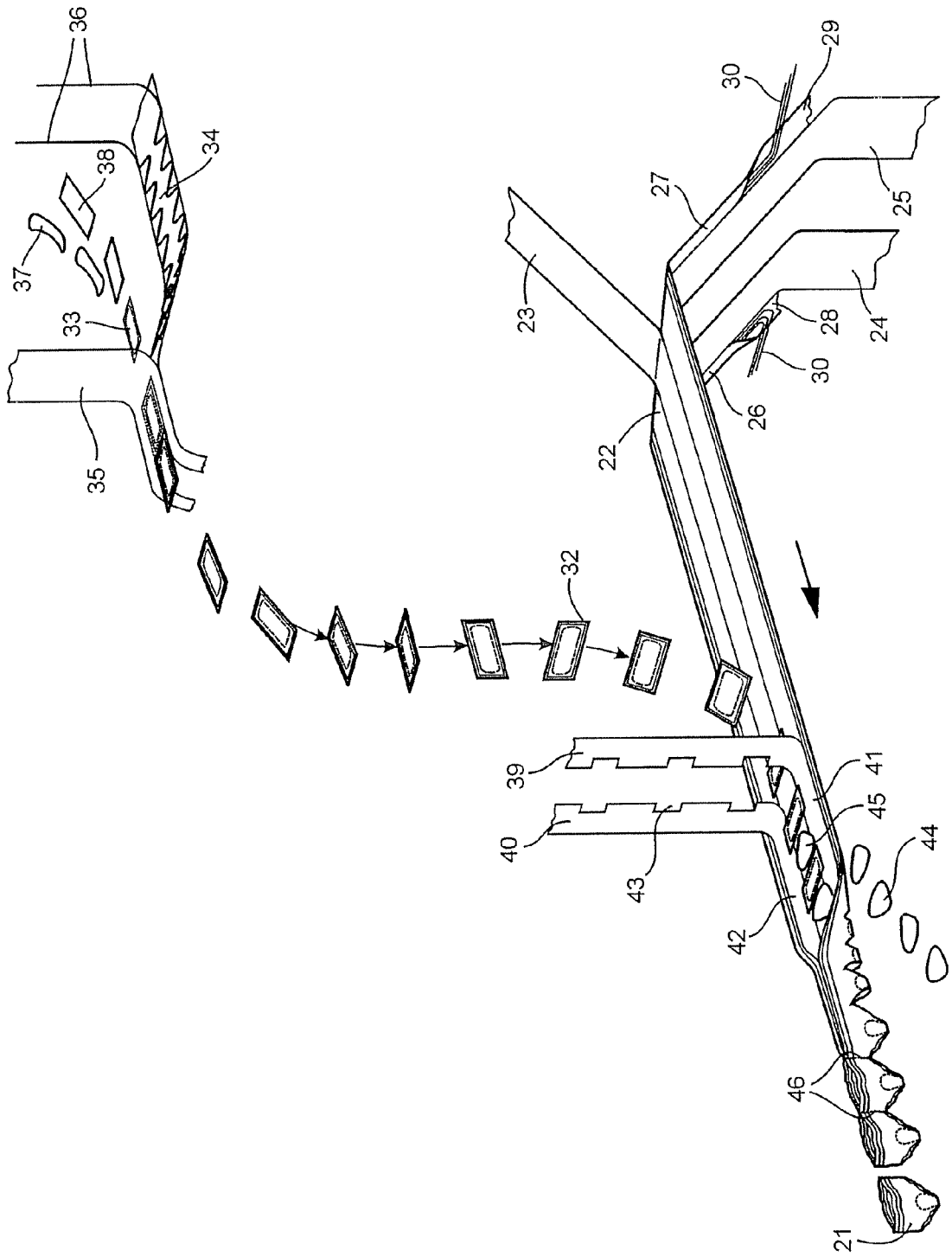
FIG. 2 shows schematically a method for producing pant-type absorbent articles.

FIG. 2 shows schematically a method for producing pant diapers 21 or other pant-type absorbent articles. In accordance with embodiments of the disclosure, the method involves forming a chassis structure carrying a core component. In all the shown embodiments of the disclosure, the core component is formed separately as a "core pack", with an absorbent core enclosed between a topsheet and a liquid impermeable backsheet. Although this is a preferred way of incorporating the core component in the chassis structure, alternative embodiments utilising parts of the chassis structure as topsheet and/or backsheet are also contemplated within the scope of the disclosure.

The preferred embodiments of the pant-forming process according to the disclosure involves using continuous webs of material to form different chassis web portions such as a crotch portion, front and back panel portions and a waist band portion, and stretching the elastic two-layer laminate webs in the machine direction, MD, as shown in the Figs. However, as previously stated, the pant-forming process according to embodiments of the disclosure may also involve the incorporation of discrete elastic laminate webs and other elements and may involve stretching of the two-layer laminate webs in the cross direction, CD, or in more than one direction.

As shown in FIG. 2, a chassis structure is formed from a compound chassis web 22 comprising a central nonwoven chassis web 23, first and second activated elastic two-layer laminate webs 24,25 and first and second waist features 26,27. The elastic two-layer laminate webs 24,25 can be webs of the laminate produced in the method shown in FIG. 1. Alternatively, the webs may be produced by means of any other suitable lamination method, such as by adhesive bonding, meltblowing, of a nonwoven web onto an elastic film, ultrasonic bonding or thermobonding. The laminate webs include one layer of an elastic film and one nonwoven layer and have been activated as previously described. The laminate webs 24,25 are joined to the central nonwoven chassis web 23 with the film side facing the viewer of FIG. 2 and with the nonwoven side facing away from the viewer. In this manner, the nonwoven side of the laminate webs will be on the outside of the finished pant diaper 21.

Before joining the laminate webs 24,25 to the central nonwoven chassis web 23, the laminate webs are stretched at least in the machine direction (MD) by 10-200% of their initial, non-stretched extension. Stretching may be carried out by passing the webs between a pair of rollers driven at different speeds. By choosing and controlling the amount of stretch, it is possible to obtain a selected elasticity in the finished chassis web. The laminate webs 24,25 are preferably stretched by 35-180% of their non-stretched extension, more preferably by 50-150% of their non-stretched extension and most preferably by 70-120% of their non-stretched extension. The laminate webs 24,25 need not be stretched to the same extent if different elasticity is desired in different portions of the chassis structure. It is also possible to use elastic laminate webs having different film/nonwoven combinations, different degrees of activation, etc.

The degree of stretching of the elastic two-layer laminate webs 24,25 during the pant-forming process is a major factor in determining the final elasticity of the portion of the chassis web 22 occupied by the two-layer laminate webs 24,25.

The waist features 26,27 are created by joining separate nonwoven strips 28,29 to the outer edges of the elastic laminate webs 24,25, attaching elastic elements 30 to the nonwoven strips 28,29 and folding and securing the nonwoven strips 28,29 over the elastic elements 30 to create elastic waistbands along the edges of the chassis web 22. The elastic waist features may alternatively be formed by folding an edge portion of one or both of the elastic laminate webs 24,25. The folded portion will have greater elastic force than a non-folded web. If desired, the folded laminate web may be supplemented with additional elastic elements. It is also possible to create a waist feature at the edge of one or both of the elastic laminate webs 24,25 by attaching elastic elements to the web and optionally covering the elastic elements with a separate nonwoven strip.

A core component 32 is produced separately from the pant-forming process and is laid down on the chassis web 22.

The core component 32 comprises an absorbent core 33 arranged between a liquid barrier layer 34 and a liquid pervious topsheet layer 35. In the shown example, the core component 32 further comprises elastic elements 36 arranged in curve-shaped patterns on the liquid barrier layer 34. The shown pattern is only intended as an example and other patterns may be used for the elastic elements 36 such as linear elastic elements. It is also possible to dispense with elastic elements in the core component 32 altogether. The absorbent core is shown as a two-component structure with an upper, smaller absorbent layer 37 and a lower somewhat larger layer 38. It is to be understood that the construction of the core component 32 and the absorbent core is by no means limiting for the disclosure. Hence, any commonly employed core concepts and materials may be used in the process according to the disclosure.

After joining of the core component 32 with the chassis web 22, first and second nonwoven webs 39,40 are laminated to the stretched first and second two-layer laminate webs 24,25, respectively to create three-layer laminate webs 41,42.

In order to avoid covering the end portions of the core component 32, the nonwoven webs 39,40 are provided with cut-outs 43 that are arranged in register with the core components 32 on the chassis web 22. However, the cut-outs 43 are an optional feature and may be omitted, as desired.

As an alternative to the previously described ways of producing a waist feature on the chassis web 22, the nonwoven webs 39,40 may be sized to extend beyond the edges of the two-layer laminate webs 24,25 and the extending portions may be elasticised and used to form waist features 26,27, along the edges of the compound chassis web 23, as previously described.

The choice of material for the first and second nonwoven webs influences the flexibility and extensibility of the created three-layer laminate. The amount of bonded area between the elastic laminate webs 24,25 and the nonwoven webs does also affect the flexibility and elasticity of the three-layer laminate. Accordingly, a large bonded area will decrease the elasticity in the final laminate while sparsely distributed bonding points will have a very small or negligible influence on the elasticity.

Lamination of the nonwoven webs 39,40 to the laminate webs 24,25 may be carried out by coating or spraying the film-side of the laminate webs 24,25 with adhesive and subsequently passing the combined webs through a bonding nip between two bonding rollers. The adhesive is preferably a thermoplastic adhesive, although other types of adhesives may be used if desired. Alternatively, ultrasonic or thermal bonding may be used in the lamination step.

The resulting three-layer laminate 41,42 is elastically stretchable and has a selected elasticity primarily depending on the elasticity of the elastic film in the two-layer laminate webs 24,25, the degree of tearing of the first nonwoven web during activation of the elastic laminate webs and the amount of stretching of the two-layer laminate webs 24,25 before bonding to the nonwoven webs 39,40. However, as set out above, the properties of the nonwoven webs with regard to flexibility and extensibility and the amount of bonding effected in the second lamination step does also influence the elasticity of the final laminate 41,42.

In the pant diaper, when the elastic laminate webs are in a relaxed condition, the three-layer laminates 41,42 will have a smooth face on the outside of the diaper and an irregular, somewhat puckered face on the inside where the nonwoven layers 39,40 are applied. This is due to the nonwoven layers 39,40 having been bonded to the two-layer laminate webs 24,25 while the two-layer laminate webs were in an elastically extended state. The non-incrementally stretched nonwoven webs provide reinforcement of the laminate, makes the laminate puncture resistant, and allows the laminate to be subjected to the pulling and stretching forces arising when putting on and taking off a pant article without breaking or tearing.

Moreover, by selecting nonwoven materials having thermoplastic properties for the nonwoven in the two-layer laminate webs and/or for the nonwoven webs supplied in the pant-forming process, the webs can be joined to other components by thermo-bonding and ultrasonic welding techniques. For example, it may be beneficial if at least one of the nonwoven layers in the three-layer laminate is substantially or completely made of thermoplastic fibres, preferably polypropylene fibres. The nonwoven layer can then be used to form side joins with good tensile strength. Since thermobonds used in side joins usually penetrate the welded materials, the orientation of the laminate with respect to the nonwoven layers is normally not crucial for obtaining a thermobonded join as long as at least one of the layers is predominantly made of thermoplastic fibres or the combination of the two layers contain sufficient thermoplastic material in order to achieve sufficient bond strength. The side joins are preferably breakable side joins, i.e. welds that may be peeled or torn apart when the pant diaper is removed.

The method shown in FIG. 2 does not include the application of leg elastic elements. However, it is of course possible to apply leg elastic if additional elastification is needed at the leg openings of the pant diaper. Leg elastic may be applied in any known manner and using any known elastic elements. One example of a suitable method of arranging leg elastics is disclosed in WO 2004/078083.

After the final lamination step, a portion 44 is cut out from the chassis web 22 between the core components 32 to create leg openings 45. The chassis web and the integrated core components 32 are then folded centrally and the web halves are joined in side joins 46 between the core components. Finally, individual pant diapers 21 are cut from the production web.

The method in FIG. 2 shows the core components being joined to the chassis web before lamination with the nonwoven webs 39,40. However, in an alternative method, the core components 32 may be joined to the chassis web after the lamination step, i.e. when the chassis web has been fully assembled. In such an embodiment it is normally not necessary to arrange cut-outs in the areas of overlap between the core components and the two-layer laminate webs 24,25.

FIG. 2 is a highly schematic representation of the method according to the disclosure. However, all individual steps, such as bonding, cutting, folding, etc. are well known and described in the art.

Figure 3:
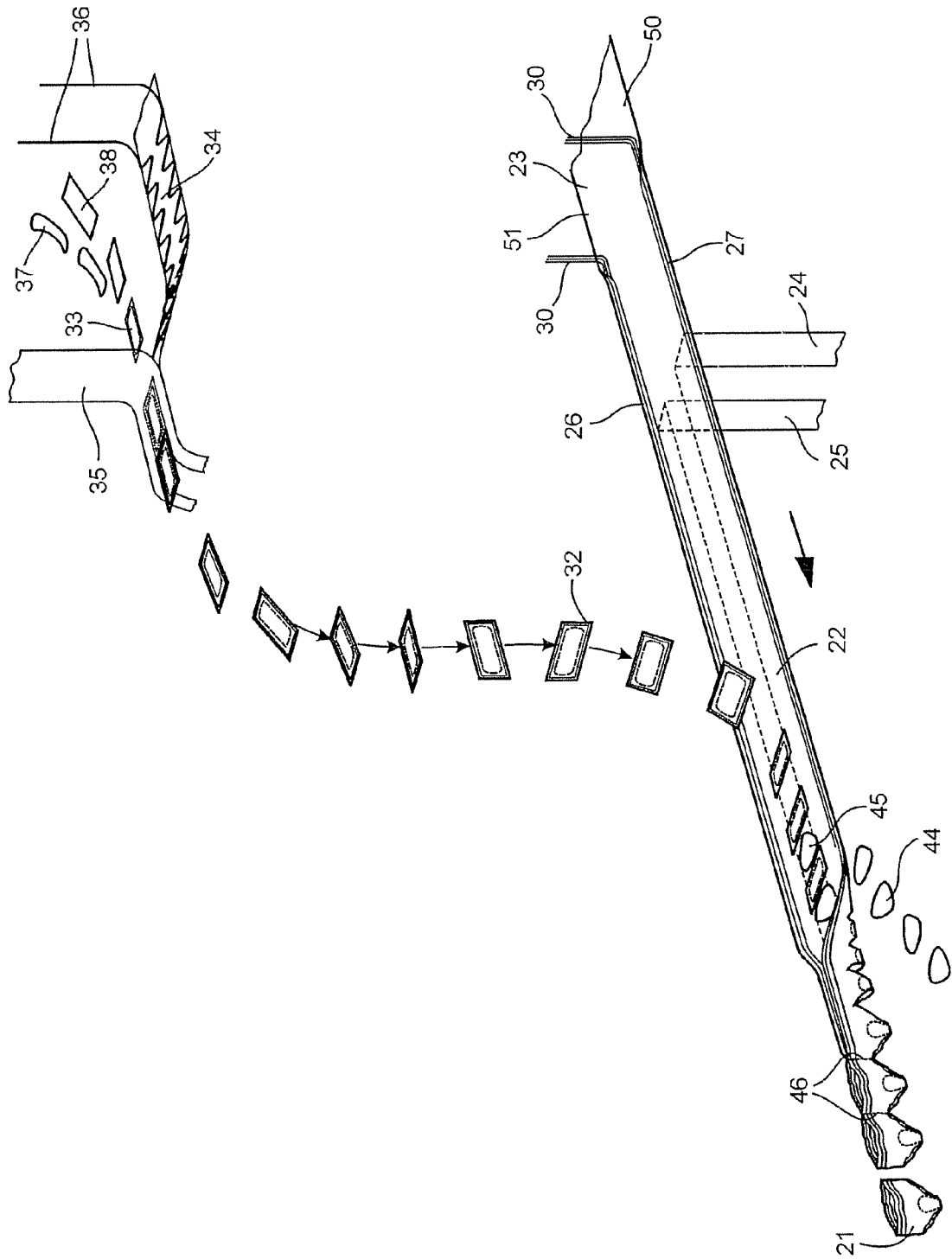
FIG. 3 shows a second embodiment of a method for producing pant-type absorbent articles.

In the method in FIG. 3, the central nonwoven chassis web 23 extends in the cross direction (CD) over the full width of the chassis web 22. Waist features 26,27 are formed in the central nonwoven chassis web 23 by attaching elastic elements 30 on edge portions 50,51 of the chassis web and folding and securing the edge portions 50,51 over the elastic elements. The direction of folding of the edge portions 50,51 is not critical to the invention. However, it is normally preferred that the edge portions 50,51 be folded in the direction shown in FIG. 3, since the free edges of the folded edge portions 50,51 will then be on the inside of the resultant pant-type article 21 and the outside will have a smoother and more tailored appearance on the outside.

First and second activated elastic two-layer laminate webs 24,25 are joined to the central nonwoven chassis web 23 with the nonwoven side facing away from the central nonwoven chassis web and with the film side facing towards the central nonwoven chassis web 23 so that the elastic film layer is sandwiched between the nonwoven layers. The elastic two-layer laminate webs 24,25 are arranged along the edges of the chassis web 23, inward of the elastic waist features and leaving a central portion of the central nonwoven chassis web 23 free from the laminate webs 24,25. In an alternative embodiment, the elastic two-layer laminate webs may be applied as a single web having no central gap. Such an embodiment produces a pant-type article having an elastic three-layer laminate covering the chassis web crotch portion, as well as the chassis web front and back panel portions.

When applied as shown in FIG. 3, the laminate webs 24, 25 will end up on the outside of the finished pant-type article 21. However, it is of course possible to arrange the laminate webs on the inside of the chassis web 23, so that the chassis web forms a continuous outer surface on the finished pant-type article 21.

As in the method in FIG. 2, the laminate webs 24,25 are stretched before lamination to the central nonwoven chassis web 23. The laminate webs are stretched at least in the machine direction (MD) by 10-200% of their initial, non-stretched extension, preferably by 35-180% of their non-stretched extension, more preferably by 50-150% of their non-stretched extension and most preferably by 70-120% of their non-stretched extension. As in the FIG. 2 embodiment, the laminate webs 24,25 need not be stretched to the same extent if different elasticity is desired in different portions of the chassis structure. Likewise, it is possible to use laminate webs having different compositions, and different degrees of activation.

The core components 32 are laid down on the assembled chassis web 22, leg cut-outs 45 are made, the production web is folded, side seams 46 are formed and the individual pant diapers 21 are severed from the production web in the same manner as in the FIG. 2 process.

The order of the production steps does not have to be as shown in FIG. 3. Accordingly, the stretched, activated two-layer laminate webs 24,25 can be laminated to the central nonwoven web 23 before forming of the waist features 26,27. Similarly, the core components 32 can be joined with the chassis web 22 before application of the two-layer laminate webs 24,25. However, in such an embodiment it may be desirable to cut away any portions of the two-layer laminate webs 24,25 that will otherwise overlap with the core components. As in the FIG. 2 method, leg elastics may be added if desired.

Figure 4:
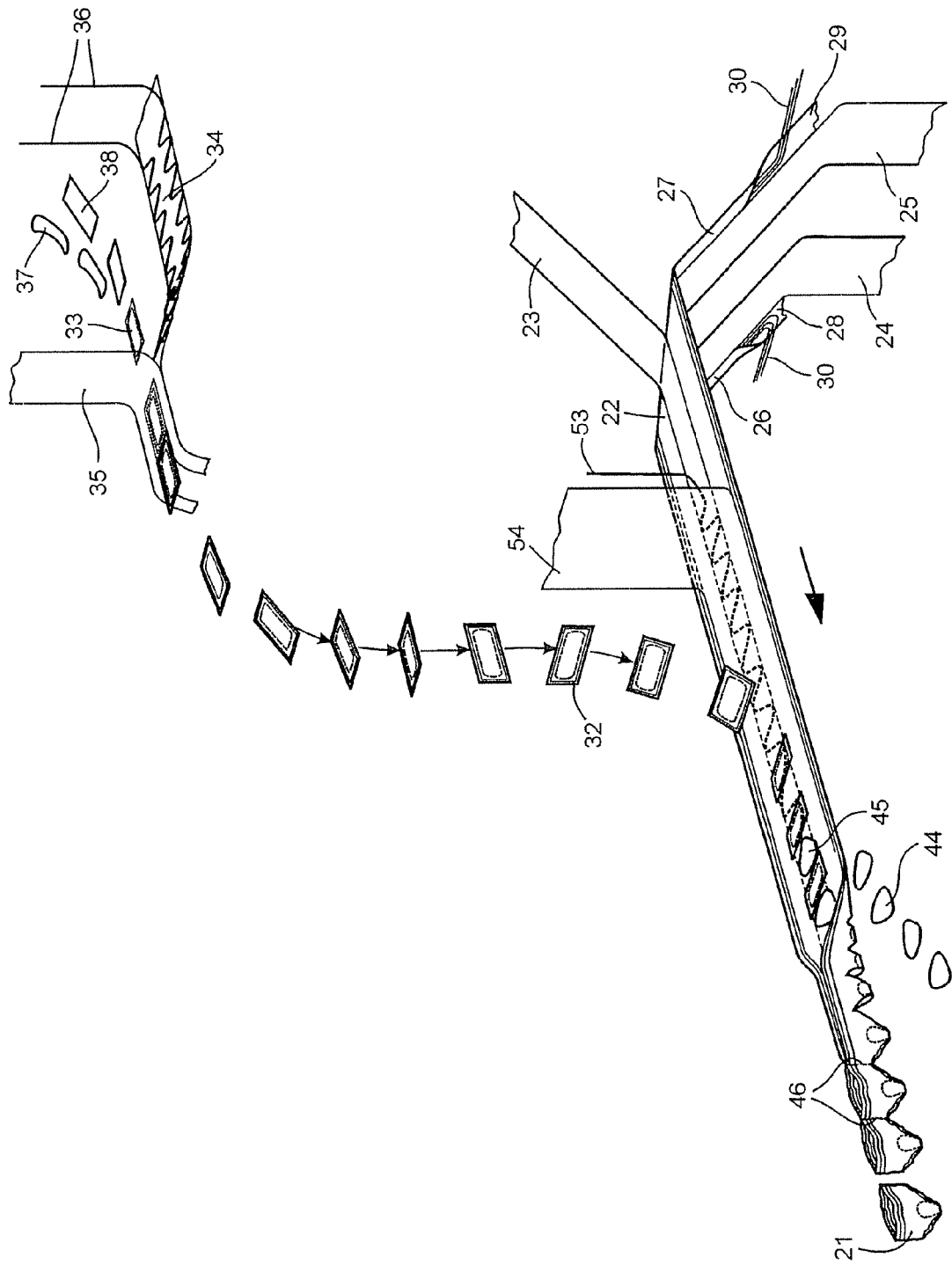
FIG. 4 shows a third embodiment of a method for producing pant-type absorbent articles.

A further method according to the disclosure is shown in FIG. 4.

As in the FIG. 2 method, the method in FIG. 4 involves forming a chassis structure from a chassis web 22 comprising a central nonwoven chassis web 23, first and second activated elastic two-layer laminate webs 24,25 and first and second waist features 26,27. The laminate webs 24,25 are joined to the central nonwoven chassis web 23 with the film side facing the viewer of FIG. 4 and with the nonwoven side facing away from the viewer so that the nonwoven side of the laminate webs will be on the outside of the finished pant diaper 21.

Before joining the laminate webs 24,25 to the central nonwoven chassis web 23, the laminate webs are stretched as previously described at least in the machine direction (MD) by 10-200% of their initial, non-stretched extension, preferably stretched by 35-180% of their non-stretched extension, more preferably by 50-150% of their non-stretched extension and most preferably by 70-120% of their non-stretched extension. Different degrees of stretching can be used for the laminate webs 24,25 if desired and the webs may have different compositions, different degrees of activation, etc.

The waist features 26,27 are created by joining separate nonwoven strips 28,29 to the outer edges of the elastic laminate webs 24,25, attaching elastic elements 30 to the nonwoven strips 28,29 and folding and securing the nonwoven strips 28,29 over the elastic elements 30 to create continuous elastic waistbands along the whole edges of the chassis web 22. The elastic waist features may alternatively be formed by folding an edge portion of one or both of the elastic laminate webs 24,25, as shown in FIG. 3, optionally supplemented with additional elastic elements. It is also possible to create a waist feature at the edge of one or both of the elastic laminate webs 24,25 by attaching elastic elements to the web and optionally covering the elastic elements with a separate nonwoven strip. Elastic waist features suitable for use in the pant-forming process in accordance with the disclosure are disclosed in PCT/SE205/000309.

Leg elastic 53 is applied to the chassis web 22 in a sinus curve pattern. The leg elastic can be any conventionally used elastic element such as one or more elastic threads, bands, etc. It is, of course possible to use further elastic elements to create leg elastic 53 and to apply the elastic elements in other patterns than the one shown herein. One suitable way of arranging leg elastic on a chassis web is disclosed in WO 2004/078083.

A core component 32 is produced separately from the pant-forming process as described in connection with FIG. 2, and is laid down on the chassis web 22 after application of the leg elastic 53.

Before joining of the core component 32 to the chassis web 22, a non-elastic or elastic nonwoven web 54 is laminated over the full width of the chassis web 22 between the waist elastic features 26,27.

As in the FIG. 2 embodiment, the core component 32 comprises an absorbent core 33 arranged between a liquid barrier layer 34 and a liquid pervious topsheet layer 35.

The nonwoven web 54 is applied to cover the central nonwoven chassis web 23, the leg elastic 53 and the two-layer laminate webs 24,25 that are joined with the central nonwoven chassis web 23.

Hence, the nonwoven web 54 will offer securement and coverage of the leg elastic members at the same time as the two-layer laminate webs 24,25 are provided with reinforcement.

Figure 5:
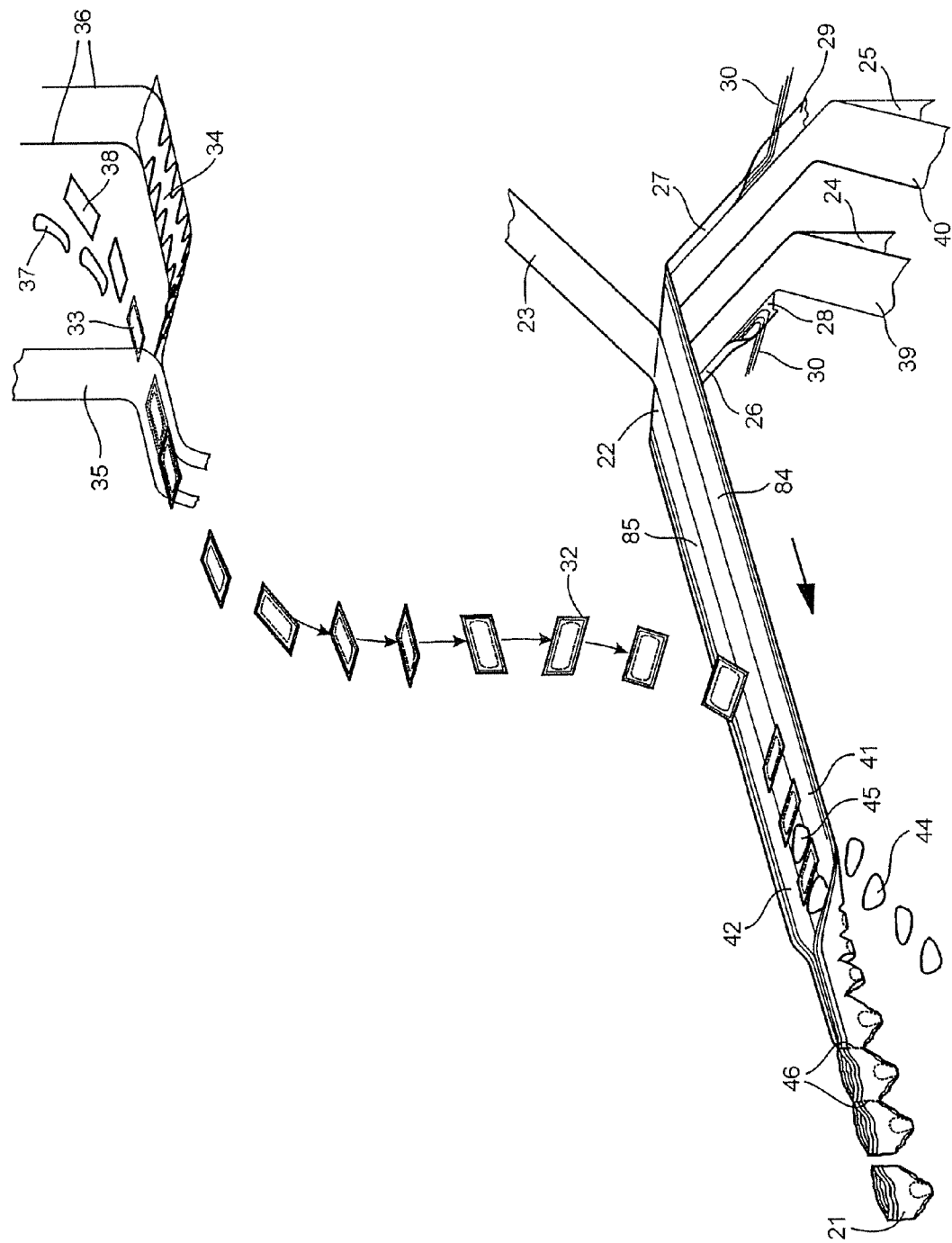
FIG. 5 shows a fourth embodiment of a method for producing pant-type absorbent articles.

A further embodiment of the method according to the disclosure is shown in FIG. 5. The FIG. 5 method is similar to that in FIG. 2, but involves applying nonwoven webs 39,40 to the stretched and activated two-layer laminate webs 24,25 before joining the thus produced elastic three-layer laminate webs 84,85 to the central nonwoven chassis web 23. As an alternative to the embodiment shown in FIG. 5, the three-layer laminate webs 84,85 may produced by laminating an activated, stretched two-layer laminate web with a nonwoven web and subsequently dividing the thus obtained three-layer laminate into two webs before joining the two webs with the central nonwoven chassis web.

Figure 6:
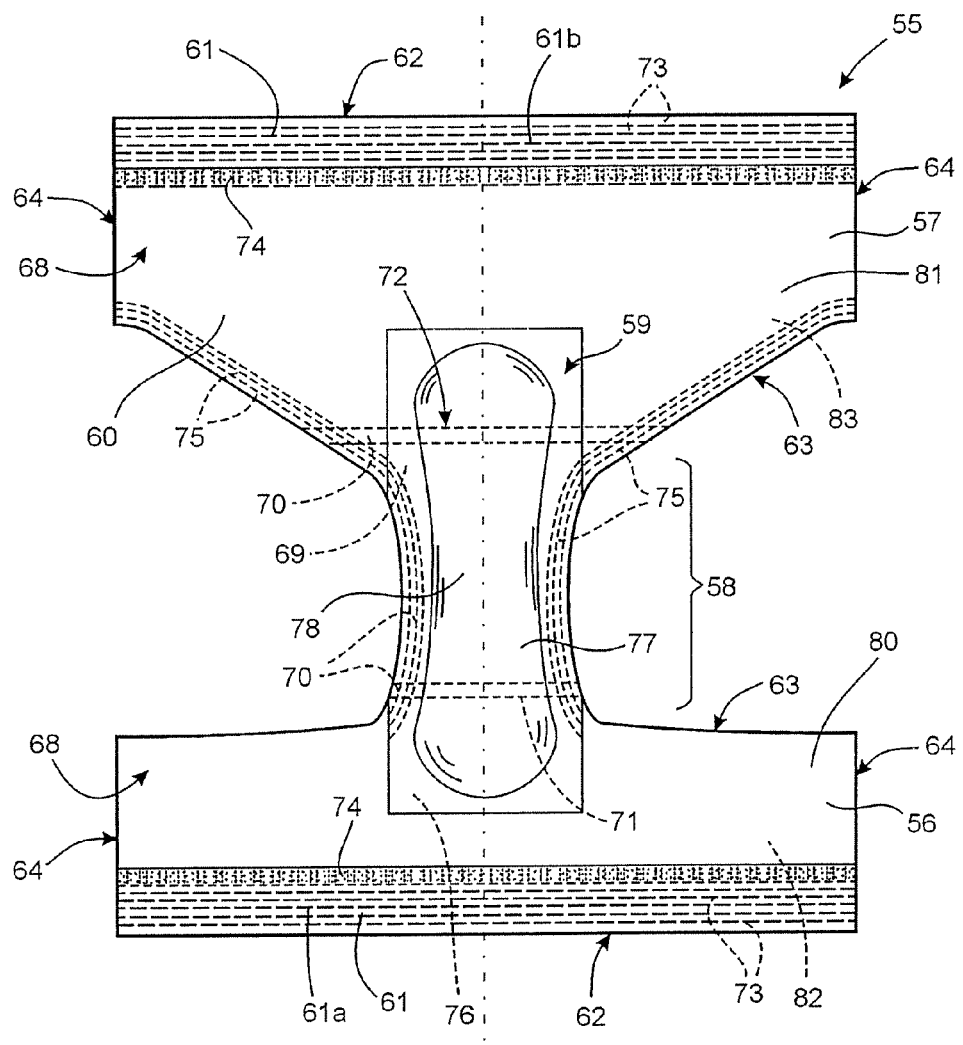
FIG. 6 shows a pant-type diaper in a flat state.
Figure 7:
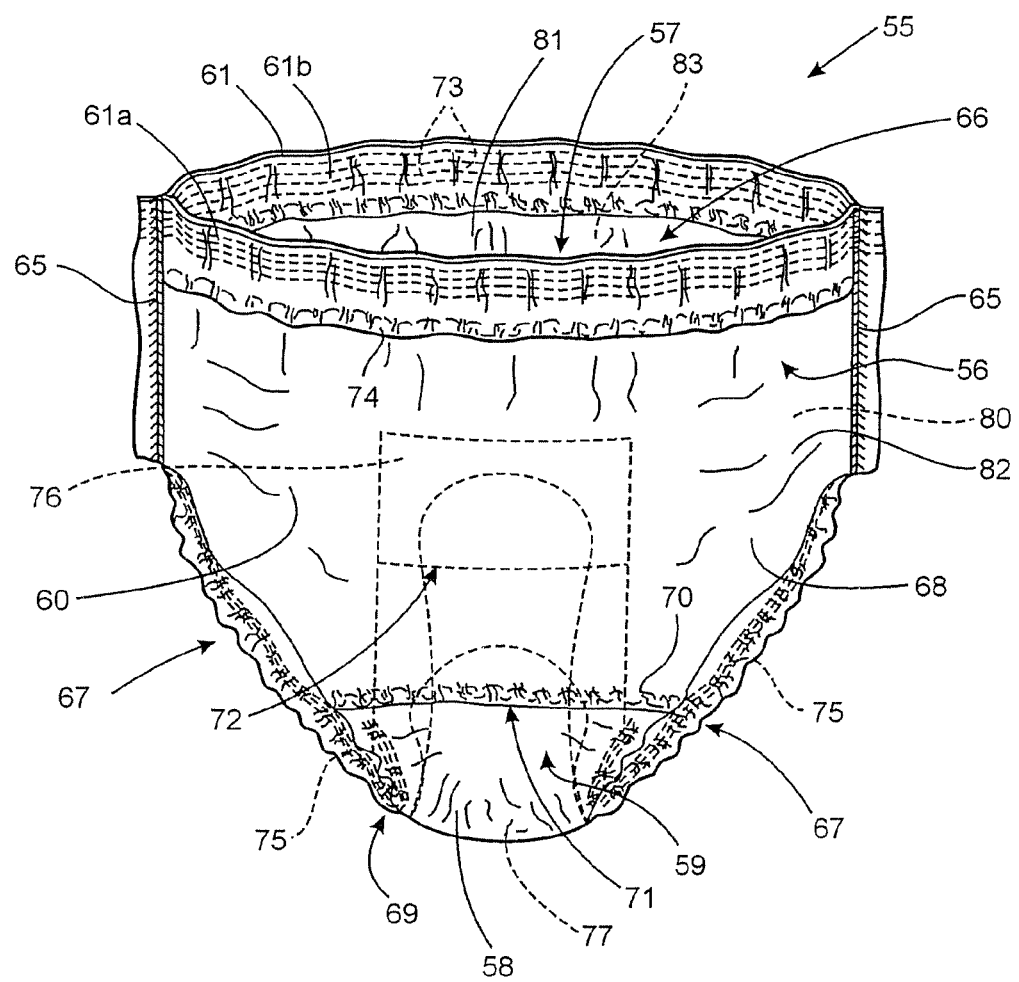
FIG. 7 shows the diaper in FIG. 3 with closed side joins.

The pant diaper 55 shown in FIGS. 6 and 7 is designed to enclose the lower part of a wearer's trunk like conventional underwear. In FIG. 6, the diaper 55 is shown from the inside, i.e. from the side facing the wearer when the article is worn and in FIG. 7, the diaper is shown from the outside, or the garment-facing side, which is the side that is facing away from the wearer when the diaper is worn.

The diaper has a front panel 56, a back panel 57 and a crotch panel 58 extending between the front and back panels 56,57 and having a relatively narrow width as compared to the front and back panels 56,57. The front and back panels 56,57 are arranged to cover the wearer's hips and to extend over the belly and the back of the wearer to encircle the lower part of the wearer's trunk.

The diaper 55 further comprises a core region 59 extending from the crotch panel 58 into the front panel 56 and the back panel 57. The front and back panels 56,57 form part of a chassis 60 that extends on the garment-facing side of the diaper 55 and covers and surrounds the core region 59. The chassis 60 comprises the front panel 56, the back panel 57 the crotch panel 58 and an elastic waist band 61 secured to the front and back panels 56,57. Each of the front and back panels 56,57 has a waist edge 62 a crotch edge 63 and a pair of side edges 64 respectively.

The term "panel" is used herein to denote a functional part of the diaper chassis while the terms "region" and "portion" are used to denote the location of a particular feature of the diaper in the chassis or to describe the intended positioning of a particular part of the diaper in relation to a user's body. A panel may be a separate component or an integrated part of the chassis. A region or portion may have an extension fully or partially covering one or more panels.

When components are joined, attached or secured to each other they are separate parts that have been bonded by any suitable means such as adhesively, by stitching or by ultrasonic welding or thermo-welding. The term joined also includes separable (openable) joins, such as separable side joins and reclosable joins such as hook-and loop joins, reclosable tape joins, snap fasteners, etc. Components that have been arranged on each other need not be bonded, although as used herein, the term "arranged" is broadly used to also include bonded components.

The front and back panels 56,57 are joined to each other along their side edges 64 by thermobonding, ultrasonic welding, glue strings or the like to form side seams 65, as shown in FIG. 7. The elastic waist band 61 consists of a front waist panel 61a and a back waist panel 61b, which are secured to the front panel 56 and the back panel 57, respectively. The front and back waist panels 61a, 61b are also joined to each other along the side seams 65. By joining the front and back panels 56, 57 and the waist panels 61a, 61b, the pant diaper 55 is provided with a waist opening 66 and a pair of leg openings 67.

FIG. 6 shows the diaper 55 in a flat state with any elastic components that are attached to the chassis 60 under tensional stress drawn out to the full non-tensioned dimensions of the chassis 60. FIG. 7 shows the pant diaper 55 as it appears when the side seams 65 have been formed and the tensioned elastic elements have been allowed to relax and gather the chassis material to form elasticized leg and waist openings 67,66.

The front and back panels 56,57 are constituted by an elastic laminate 68 comprising a two-layer film/nonwoven laminate that has been activated and stretched by 10-200%, preferably by 35-180% and most preferably by 70-120% in at least one direction and subsequently laminated to a non-elastic chassis component in the form of a nonwoven layer that is arranged on the inside of the diaper. The front and back panels 56,57 are preferably elastically stretchable at least in the direction of the waist edges 62 but may also be elastically stretchable perpendicular to the waist edges 62, in the direction of the side edges 64. Hence, each of the front and back panels 56,57 comprise an activated, stretched two-layer elastic laminate web 82,83 and a non-elastic or elastic nonwoven web 80,81. The two-layer laminate and the nonwoven web are laminated to each other with the elastic film layer of the two-layer laminate between the nonwoven web layers. The nonwoven web layers 80,81 have been laminated to the two-layer laminate webs 82,83 after activation of the two-layer laminate webs. Hence, the nonwoven web layers have not been subjected to incremental stretching and retain their initial integrity, thus providing reinforcement to the activated laminate.

The crotch panel 58 is formed from a nonwoven crotch material 69 that has been joined to the front and back panels 56,57 at crotch seams 70. Hence, the crotch material 69 which preferably is a non-elastic material, such as a non-elastic nonwoven material, is arranged in the core region 59 of the article and overlaps slightly with the elastic front and back panels 56,57. The crotch material 69 is joined along its transverse edges 71,72 to the front and back panels 56,57 at the overlapping portions. The joining can be made in any suitable way such as by ultrasonic welding, adhesively or similar. In alternative embodiments of the disclosure, an outer nonwoven material may extend continuously over the front and back panels 56, 57 and the crotch panel 58 so that no seams or joins are needed between the panels 58,56,57.

In the shown example, the elastic waist band 61 comprises first and second plies of substantially non-elastic nonwoven material that is elasticized by one or more elongate elastic members 73, such as elastic threads or bands. The first and second plies can be formed from a single layer of material that is folded over onto itself or can be made from two separate strips of material. The elastic members 73 are arranged in the waist band 61 in a tensioned state such that they contract and gather the nonwoven material in the waist band 61 when they are allowed to relax, as shown in FIG. 7.

The elastic waist band 61 is secured to the front and back panels 56,57 with the elastic members 73 in an extended state and with the material in the front and back panels sandwiched between the nonwoven plies in the waist band. Alternatively, the elastic waist band 61 can be a component that is prefabricated and joined to the outside or the inside of the front and back panels 56,57 respectively. The waist band join 74 between the waist band 61 and the front and back panels 56,57 can be made in any suitable way such as by means of ultrasonic welding, heat welding, or adhesively. A further option is to create the waist band 61 from one or more non-elastic nonwoven layers that are also parts of the front and back panels 56,57 and form continuous extensions thereof. It is also conceivable to form an elastic waist feature by double-folding portions along the waist edges 62 of the elastic front and back panels 56,57 and optionally supplementing the folded portions by additional elastic elements.

Elastic members 75 are also arranged at the edges of the leg openings 67 and serve to elasticize the leg openings. The elastic members at the leg openings can be any kind of conventional elastic elements such as elastic threads, bands, foam strips, or similar.

The planar extension of the core region 59 is defined by a liquid-impervious barrier sheet 76 arranged between an absorbent core 77 and the chassis 60. The liquid-impervious barrier sheet 76 has rectangular shape and the absorbent core 77 is hour-glass shaped. A liquid permeable topsheet 78 is arranged over the core 77 and the liquid-impervious barrier sheet 76. Hence, the liquid-impervious barrier sheet 76 underlies the absorbent core 77 and the adjacent areas immediately outside the absorbent core 77.

The liquid-permeable topsheet 78 can consist of any material known for the purpose, such as a layer of nonwoven material, a perforated plastic film, net material, tow, or the like. The topsheet 78 can, of course, also consist of a laminate of two or more sheets of the same or different material.

The liquid-impervious barrier sheet 76 can consist of a liquid-impermeable plastic film, a nonwoven sheet which has been coated with a liquid barrier material, or some other flexible material sheet which has the ability to withstand liquid penetration. However, it can be advantageous if the liquid-impervious barrier sheet 76 has a certain breathability, i.e. permits the passage of water vapour through the sheet 76.

The absorption core 77 can be made up of absorbent material, such as cellulose fluff pulp, tissue, absorbent foam, etc. It is also possible for the absorption core to contain superabsorbents, i.e. polymer materials which are able to absorb body fluid corresponding to many times their own weight and form a hydrogel. Such superabsorbents are usually present in the form of particles, but fibres, flakes, granules and films are also available. Moreover, the absorption core 77 can comprise nonabsorbent components such as stiffening elements, shaping elements, binders, etc. Various types of liquid-receiving porous structures such as fibre wads, open-cell foam or the like can also be included in the core.

The topsheet 78, barrier sheet 76 and absorption core 77 can be produced as a separate component or "core pack" that is subsequently integrated in the diaper chassis as shown in FIGS. 2-5. The various components included in the core pack can be connected to one another in a conventional manner, for example by adhesive bonding, ultrasonic welding or thermowelding. The core pack can of course contain further components in addition to those described here, for example the core pack can comprise a liquid transport sheet, elastic members, shape-stabilizing members, shaping elements or the like.

In the embodiment shown in FIGS. 6 and 7, the core pack has been integrated with the chassis after the chassis has been fully assembled. Alternatively, the core pack can be applied to the chassis before lamination of the nonwoven webs 80,81 to the elastic two-layer laminate webs in the front and back panels 56,57. It may then be desirable to provide the nonwoven webs 80,81 with cut-outs arranged in the areas of the nonwoven webs 80,81 that would otherwise be covering the absorbent core 77.

The nonwoven material 69 in the crotch panel 58 is arranged on the garment-facing side of the liquid-impervious barrier sheet 76. The core region 59 extends into the front and back panels 56,57 so that the elastic laminate 68 in these panels overlap with the liquid-impervious barrier sheet 76 in the outer parts of the core region 59 as seen in FIG. 3. The elastic laminate 68 is arranged on the garment-facing side of the liquid-impervious barrier sheet 76.

As shown in FIGS. 6 and 7, an elastic three-layer laminate 68 comprising an activated, stretched elastic two-layer film/nonwoven laminate and a non-elastic non-activated nonwoven layer, preferably forms the front and the back panels 56,57 of the pant diaper 55. However, it is possible to make only parts of the respective front and back panels 56,57 of the elastic three-layer laminate 68. In such embodiments, at least 20%, preferably at least 25%, more preferably at least 30% and most preferably at least 40% of the total surface area of the chassis as seen in the flat state shown in FIG. 6 is constituted by an elastic three-layer laminate resulting from a pant-forming process in accordance with the disclosure. As an example, the elastic laminate may be used only in those parts of the front and back panels 56,57 that are intended to lie over the wearer's hips and thus form elastic side panels. It is also possible to design a pant article without any overlap between the core region 59 and the elastic laminate material in the front and back panels 56,57.

The three-layer laminate 68 in the front and back panels 56,57 is arranged with the nonwoven web of the two-layer elastic laminate on the outside of the diaper and with the additional nonwoven web of the inside of the diaper. This implies that the diaper, when in a relaxed state, will have a smooth outside and a slightly corrugated or micropleated inside. If desired, the orientation of the three-layer laminate can be reversed so that the smooth side is on the inside of the diaper and the corrugated side is on the outside.

In an embodiment with the additional nonwoven arranged on the outside, the nonwoven can be in the form of a single web extending the whole distance between the waist bands 61, thus constituting a full, seamless outer diaper cover. Further, when using a continuous outer cover web, there is no need to apply a separate crotch nonwoven web 69 since the cover nonwoven will also form the crotch panel 58.

It is also conceivable to arrange a continuous nonwoven layer on the inside of the diaper covering and being laminated to the elastic front and back panels 56,57 and forming the crotch panel 58. This embodiment is beneficial in that it allows the nonwoven layer to also cover and secure any leg elastic 75 present in the front and back panels 56,57.

The disclosed and shown pant-forming methods in FIGS. 2-5 should be understood as only being examples of the method in accordance with the disclosure. Hence, the different method steps may be carried out in different order from that described, as explained above. Moreover, the embodiments of method in accordance with the disclosure cover all embodiments wherein a pre-fabricated, activated elastic two-layer film/nonwoven laminate is introduced in a pant-forming process and incorporated as a part of a compound chassis web. Accordingly, the two-layer laminate may be used to elasticise any portion of the compound chassis web, such as the crotch panel portion, the front and/or back panel portion, and the waist panel portions. One or more two-layer laminate webs may be introduced in the pant-forming process. The nonwoven chassis web to which the two-layer elastic laminate is laminated may have portions that are not elasticised by the two-layer elastic laminate. Such non-elasticised portions of the nonwoven chassis web may be used to form a waist feature, a non-elastic crotch panel portion, non-elastic portions in registry with the absorbent core component, etc.

The pant-forming process may include application of further features such as elasticised or non-elasticised barriers, lotion, odour control agents, shaping elements, stabilising elements, etc.

Description of Test Methods

Tensile Strength (Reference: ASTM D 882)

The method measures tensile strength and elongation of different elastic materials. The tensile strength and elongation of a well-defined test piece is tested by means of a tensile tester.

Apparatus: Instron 456
  Tensile tester connected to a computer
  Crosshead speed: 500 mm/min
  Clamp distance: 50 mm
  Sample preparation: Test samples are cut from the entire width of the material. The width of the sample shall be 25.4 mm and the length at least 50 mm longer than the clamp distance if possible. It is of importance that the edges of the sample are even and without break notches. The samples are conditioned for at least 4 h in 50% RH±5% RH and 23° C.±2° C. before testing.
  Procedure: The tensile tester is calibrated according to the apparatus instructions and set to zero. The sample is mounted and it is ensured that it is not obliquely or unevenly fastened. The material is prevented from slipping by using clamps covered with galloon or similar material. The tensile tester is started, and stopped after the material has broken (if not automatically controlled). Measurements resulting from premature failure (i.e. the sample breaks at the clamp, or is damaged during preparation) are ignored, if possible.

The following results are expressed by the tensile tester/computer:
  Maximum force, N/25.4 mm
  Elongation at maximum force, %
  Break force, N/25.4 mm
  Elongation at break force, %
  Knee point, N/%

Elasticity Test

The method measures how an elastic material behaves at cycles of repeated load and unload. The sample is stretched to a predetermined elongation and a cyclic movement between 0 and said predetermined elongation is performed. Desired load and unload forces are recorded. The permanent, i.e. remaining, elongation of the relaxed material is measured.

A tensile tester, Lloyd LRX, able to perform cyclic movements and equipped with a printer/plotter or software presentation is used. The sample is prepared by cutting it to a width of 25 mm and a length that is preferably 20 mm longer than the distance between the clamps in the tensile tester.

The tensile tester is calibrated according to the apparatus instructions. The parameters needed for the test (load and unload forces) are adjusted to:

| | |
|---|---|
| Crosshead speed: | 500 mm/min |
| Clamp distance: | 50 mm |
| Preload: | 0.05 N |

The sample is placed in the clamps according to the marks and it is made sure that the sample is centred and fastened perpendicularly in the clamps. The tensile tester is started and three cycles between 0 and the predetermined elongation equal to the highest defined $1^{st}$ load are performed. Before the last cycle, the sample is relaxed for 1 minute, then the permanent elongation is measured by stretching the sample until a force of 0.1 N is detected and the elongation is read.

An elastic material is defined as a material having a permanent elongation after relaxation of less than 10% after the material has been subjected to an elongation of 30% in the test above. An elongation of 30% means an elongation to a length that is 30% longer than the initial length of the sample.

A non-elastic material has a permanent elongation after relaxation of more than 10% after having been subjected to an elongation of 30%.

Puncture Strength

Puncture strength is measured according to ASTM Designation D3763-02. From penetration impact-type tests, this method produces data of load versus displacement. The maximum load for each sample is calculated.

EXAMPLES

The tensile strength in the machine direction (MD) and the cross direction (CD) was measured for three samples.

Sample A is a conventional activated three-layer laminate comprising an inner apertured three-layer elastomeric film of PE-SEBS-PE, basis weight 36 g/m$^2$ and two outer layers of spunbond material, PP (polypropylene), each having a basis weight of 22 g/m$^2$. The laminate was produced by applying one spunbond layer to the film while the film was in a tacky state and the other spunbond layer was adhesively laminated to the film layer using, for example, a pressure sensitive hot melt adhesive (glue amount 3 g/m$^2$). The laminate was incrementally stretched, at which the non-elastic spunbond layers were stretched to a point below the elongation at maximum load to retain some strength in the spunbond layers.

The basis weights of the layers in the laminate are the basis weights after activation. Before activation, the basis weight of the individual layers was: inner film layer 40 g/m², outer spunbond layers 25 g/m² each and glue layer 3 g/m².

Sample B is a three-layer laminate comprising a first activated bi-laminate comprising a spunbond nonwoven PP layer having a basis weight of 22 g/m² and an apertured three-layer elastomeric film of PE-SEBS-PE, basis weight 36 g/m² that has been further laminated under stretching by 70% with a spunbond nonwoven layer having a basis weight of 18 g/m² (S1800PHW from Union Industries SpA).

Sample C is a three-layer laminate comprising the activated bi-laminate of Sample B that has been further laminated under stretching by 70% with a spunbond nonwoven layer having a basis weight of 20 g/m². (Lutrasil 9520XF from Freudenberg Fliesstoffe KG).

Sample D is a three-layer laminate comprising the activated bi-laminate of Sample B that has been further laminated under stretching by 25% with a creped nonwoven spunbond having a basis weight of 20 g/m². (From First Quality) The creped nonwoven was compacted to 50% at creping.

Sample E is the same three-layer laminate as in Sample D but with the bi-laminate stretched by 40% during lamination with the creped nonwoven layer.

The test results are shown in Table 1, below.

TABLE 1

| Sample | Tensile strength MD N/25 mm | Tensile strength CD N/25 mm | Puncture force N |
| --- | --- | --- | --- |
| A | 34 | 9 | 40 |
| B | 42 | 26 | 74 |
| C | 40 | 33 | 80 |
| D | 25 | 38 | 73 |
| E | 22 | 44 | 77 |

As can be seen in Table 1, the laminates B-E in accordance with the disclosure has considerably higher MD and CD tensile strength and higher puncture resistance than the prior art three-layer laminate.

The invention should not be considered as limited by the above description; rather the scope and limitations of the invention are defined by the enclosed claims, and equivalents thereof.

The invention claimed is:

1. A method for producing pant-type absorbent articles each article including a chassis structure having at least one elastic panel and an integrated absorbent core component, the method including a continuous pant-forming process comprising forming the chassis structure and incorporating the absorbent core component into the chassis structure, wherein the at least one elastic panel is produced by
   a) separately producing a two-layer laminate comprising a first non-elastic fibrous nonwoven web and an elastic film,
   b) activating the two-layer laminate by incremental stretching in at least one activation direction to render the two-layer laminate elastically stretchable,
   c) stretching the activated two-layer laminate by 35-200% in the activation direction,
   d) introducing the two-layer laminate in the pant-forming process, and
   e) laminating the elastic film of the stretched two-layer laminate to a nonwoven chassis component, wherein the elastic film of the stretched two-layer laminate is in direct contact with the nonwoven chassis component.

2. The method according to claim 1, wherein the nonwoven chassis component is a non-elastic component.

3. The method according to claim 1, wherein the core component is formed separately from the pant-forming process and introduced in the pant-forming process before or after lamination the elastic film to the nonwoven chassis component.

4. The method according to claim 1, wherein the pant-forming process comprises:
   a) laminating the elastic film side of a first web of the activated, stretched two-layer laminate to a first portion of a continuous nonwoven chassis web, and
   b) laminating the elastic film side of a second web of the activated stretched two-layer elastic laminate to a second portion of the continuous nonwoven chassis web to form a compound chassis web.

5. The method according to claim 4, wherein the pant-forming process comprises:
   a) laminating the first web of the activated stretched two-layer elastic laminate to a first portion of the continuous nonwoven chassis web at a distance from a first edge on the continuous nonwoven chassis web
   b) laminating the second web of the activated, stretched two-layer laminate to a second portion of the continuous nonwoven chassis web at a distance from a second edge on the continuous nonwoven chassis web
   c) forming an elastic waist feature along the first and second edges of the continuous nonwoven chassis web by joining elastic means to the continuous nonwoven chassis web at a first edge portion between the first edge of the continuous nonwoven chassis web and the first web of the activated stretched two-layer elastic laminate and at a second edge portion between the second edge of the continuous nonwoven chassis web and the second web of the activated stretched two-layer elastic laminate and by folding the first and second edge portions of the continuous nonwoven chassis web to enclose the elastic means.

6. The method according to claim 1, wherein the pant-forming process comprises:
   a) producing first and second three-layer elastic laminate webs by laminating an activated, stretched two-layer laminate to a nonwoven web,
   b) joining the first web of the three-layer elastic laminate to a first edge of a continuous central nonwoven chassis web, and
   c) joining the second web of the three-layer elastic laminate to a second edge of the continuous central nonwoven chassis web to form a compound chassis web.

7. The method according to claim 1, wherein the pant-forming process comprises:
   a) joining a first web of the activated, stretched two-layer laminate to a first edge of a continuous central nonwoven chassis web,
   b) joining a second web of the activated stretched two-layer elastic laminate to a second edge of the central nonwoven chassis web to form a compound chassis web,
   c) attaching a leg elastic member to the compound chassis web, and
   d) laminating a nonwoven web to the compound chassis web, the nonwoven web covering the first and second two-layer elastic laminate webs and the leg elastic member.

8. The method according to claim 1, wherein the pant-forming process comprises:
   a) laminating a first web of the activated stretched two-layer elastic laminate to a portion of a first continuous nonwoven chassis web at a distance from a first edge on the first continuous nonwoven chassis web,
b) laminating a second web of the activated, stretched two-layer laminate to a portion of a second continuous nonwoven chassis web at a distance from a first edge on the second continuous nonwoven chassis web, and
c) joining the first edge on the first continuous nonwoven chassis web to the first edge on the second continuous nonwoven chassis web to form a compound chassis web.

9. The method according to claim 1, wherein the at least one elastic panel is provided with an elastic waist feature along at least one edge.

10. The method according to claim 9, wherein the elastic waist feature is joined to the at least one elastic panel as a separate component.

11. The method according to claim 9, wherein the elastic waist feature is an integral part of the at least one elastic panel.

12. The method according to claim 1, wherein the pant-forming process comprises:
a) laminating the web of the activated stretched two-layer elastic laminate to the continuous nonwoven chassis web at a distance from the edges of the continuous nonwoven chassis web,
b) forming an elastic waist feature along the first and second edges of the continuous nonwoven chassis web by joining elastic means to the continuous nonwoven chassis web at a first edge portion between the edge of the continuous nonwoven chassis web and a first edge on the web of the activated stretched two-layer elastic laminate web, and at a second edge portion between a second edge of the continuous nonwoven chassis web and a second edge of the activated stretched two-layer elastic laminate web and by folding the first and second edge portions of the continuous nonwoven chassis web to enclose the elastic means.

13. The method according to claim 1, wherein the activated two-layer laminate is stretched in the activation direction by 70-180% of its non-stretched extension, during lamination with the nonwoven chassis component.

14. The method according to claim 1, wherein the pant-forming process further includes one or more of the following production steps:
a) cutting a chassis web to form leg openings,
b) folding the chassis web together with the integrated absorbent core component,
c) forming side joins in the folded web, and
d) separating individual pant-type absorbent articles from the chassis web by cutting at the side joins.

15. The method according to claim 1, wherein the pant-type absorbent article comprises a front panel, a back panel and a crotch panel attached directly to the front and back panels, and wherein at least part of the front, back or crotch panel comprises the at least one elastic panel.

16. A pant-type absorbent article comprising a chassis structure comprising a front panel having a front end edge and first and second side edges, a back panel having a back end edge and first and second side edges and a crotch panel arranged between the front and back panels and front and back waist panels arranged at the front and back panels respectively, and a core component being integrated with the chassis structure, the first and second side edges of the front panel being joined by edge joins to the corresponding first and second side edges of the back panel,
wherein at least one of the front and back panels comprises an activated two-layer elastic laminate comprising a first non-elastic fibrous nonwoven web and an elastic film and a nonwoven chassis component that has been laminated to the elastic film of the two-layer elastic laminate after activation in at least one activation direction and while the two-layer elastic laminate was stretched by 35-200%, of its non-stretched extension in the activation direction, wherein the elastic film of the two-layer elastic laminate is in direct contact with the nonwoven chassis component.

17. The pant-type absorbent article according to claim 16, wherein an elastic waist panel is arranged on at least one of the front and back panels.

18. The pant-type absorbent article according to claim 16, wherein the elastic waist panel extends continuously all the way between the edge joins.

19. The pant-type absorbent article according to claim 16, wherein at least 20% of the total surface area of the chassis as seen in a flat state is constituted by an elastic three-layer laminate comprising the activated two-layer elastic laminate and the nonwoven chassis component that has been laminated to the two-layer elastic laminate.

20. The pant-type absorbent article according to claim 16, wherein the nonwoven chassis component is a creped nonwoven web.

21. The pant-type absorbent article according to claim 16, wherein the core component comprises a topsheet, a barrier sheet and an absorption core between the topsheet and the barrier sheet.

22. The pant-type absorbent article according to claim 16, wherein the crotch panel is separate from the front and back panels, and the crotch panel is attached to the front and back panels.

* * * * *